United States Patent [19]

Barngrover et al.

[11] Patent Number: 5,733,776
[45] Date of Patent: Mar. 31, 1998

[54] CONTINUOUS SETTLING APPARATUS

[75] Inventors: Debra A. Barngrover, Wayland; William J. Jacobsen, North Grafton; Dimitri P. Nicolakis, Revere; James E. Fleury, Bellingham, all of Mass.

[73] Assignee: Genzyme Corporation, Cambridge, Mass.

[21] Appl. No.: 149,444

[22] Filed: Nov. 9, 1993

[51] Int. Cl.$^6$ .................................................. C12M 1/36
[52] U.S. Cl. ............................. 435/286.5; 435/286.7; 435/289.1; 210/532.1; 210/533
[58] Field of Search .................... 435/287, 289, 435/299, 813, 304, 286; 210/532.1, 536, 533, 219

[56] References Cited

U.S. PATENT DOCUMENTS

| | | | |
|---|---|---|---|
| 4,329,433 | 5/1982 | Seebeck et al. | 435/313 |
| 4,335,215 | 6/1982 | Tolbert et al. | 435/241 |
| 5,100,801 | 3/1992 | Ward, Jr. et al. | 435/813 |
| 5,166,072 | 11/1992 | Krauling et al. | 435/313 |
| 5,169,781 | 12/1992 | Nojima et al. | 435/284 |

OTHER PUBLICATIONS

Lassen, K. et al. (1992) "Methods for Cell Separation Based on Sedimentation", *Biotechnology Techniques*, 6(2):121–126.

Kitano, K. et al. (1991) "Effective Production of Anti–Tetanus Toxoid and Anti–HBsAg Human Monoclonal Antibodies by Serum–free Culture of Hybridomas" *Cytotechnology*, 5:S53–74.

Hosoi, S. et al. (1991) "Optimization of Cell Culture Conditions for Production of Biologically Active Proteins" *Cytotechnology*, 5:S17–34.

Mohan, S. et al. (1991) "Passive Release of Monoclonal Antibodies from Hybridoma Cells", *Cytotechnology*, 5:201–209.

Hoshino, K. et al. (1990) "Continuous Ethanol Production from Raw Starch Using a Reversibly Soluble–Autoreciprocating Amylase and Flocculating Yeast Cells", *J. Fermentation and Bioengineering*, 69(4):228–233.

Wells, J.R. et al. (1990) "Mammalian Cell Separation Using Unit Gravity Sedimentation", ABL, 8(1): 1990.

Tyo, M. et al. (1989) "Novel High Density Perfusion System for Suspension Culture Metabolic Studies", *1989 Mtg. New Developments in Mammalian Cell Reactor Studies*.

Takazawa, Y. et al. (1989) "High Cell Density Perfusion of Mouse–Human Hybridomas", *Appl. Microbiol. Biotech.*, 32:280–284.

(List continued on next page.)

*Primary Examiner*—James C. Housel
*Assistant Examiner*—Jan M. Ludlow
*Attorney, Agent, or Firm*—William G. Gosz

[57] ABSTRACT

An apparatus for suspending particles in a continuous flow of liquid. The apparatus comprises: 1) an agitation vessel, containing particles suspended in the liquid, wherein the density of each particle is greater than the liquid density; 2) a flow source for the continuous flow of liquid into the agitation vessel; 3) a first variable inlet/outlet for allowing the periodic free flow of a portion of the particle suspension between the agitation vessel and a settling vessel; 4) a second variable inlet/outlet for allowing the free flow of a portion of the particle suspension between the agitation vessel and the settling vessel; 5) a settling vessel located above the agitation vessel which has: i) a body for allowing the settling of the particles whereby the particles separate from a portion of the liquid; and ii) an outlet for allowing the removal of liquid; and 6) a vacuum source for drawing a portion of the particle suspension into the settling vessel and for periodically removing a portion of the liquid out of the settling vessel, whereby a continuous flow of the liquid enters into the apparatus and a portion of the liquid periodically exits the apparatus wherein the liquid exiting the apparatus is particle free. In addition, the apparatus of the present invention is suitable for growing particles or for separating liquids of different densities.

16 Claims, 3 Drawing Sheets

OTHER PUBLICATIONS

Tokashiki, M. et al. (1989) "High Density Culture of Mouse–Human Hybridoma Cells Using a Perfusion Culture . . ." *Cytotechnology*, 2:5–8.

Takazawa, Y. et al. (1989) "Production of Human–Mouse Chimeric Antibody by High Cell Density Perfusion Culture", *Cytotechnology*, 2:95–101.

Kitano, K. et al. "Production of Human Monoclonal Antibodies by Heterohybridomas", *Appl. Microbiol. Biotech.*, 24:282–286.

Davison, B.H. et al. (1985) "Stable Competitive Coexistence in a Continuous Fermentor with Size–Selective Properties", 1(4):260–268.

Yonezawa, Y. (1984) "Recycle Continuous System for Mss Propagation of Animal Cells", Growth and Differentiation *Cells in Defined Environment*, Proceedings of Int'l Symposium, Fukuoka, Japan.

Sato, S. et al. (1984) "Production of Interferon and Monoclonal Antibody Using a Novel Type of Perfusion Vessel" *Growth and Differentiation of Cells in Defined Environment*, Proceedings of Int'l Symposium, Fukuoka, Japan.

Butler, M. et al. (1983) "High Yields from Microcarrier Cultures by Medium Perfusion", J. Cell Sci., 61:351–363.

CONTINUOUS SETTLING APPARATUS

BACKGROUND OF THE INVENTION

Since the development of the in vitro cultivation of cells the demand for large scale production of these cells and the products they express has increased. There is an increasing interest to use in vitro cultivated cells as recombinant hosts for the production of cellular products as potential diagnostic and therapeutic agents because for many of these agents, cell culture systems provide the only viable production source. These useful agents include monoclonal antibodies, human growth hormones, lymphokines, erythropoietin, blood clotting factors, and tissue plasminogen activators.

Cells, in particular mammalian, have the capability to synthesize these agents with the proper configuration, correct disulfide bonding, and arrays of sugar side chains which result in the desired activity of the naturally occurring agent. Therefore, many agents derived from cells are more likely to be efficacious and are less likely to be immunogenic in mammals if expressed by mammalian cells than if produced by bacterial or yeast fermentation.

Continuous suspension cell culture systems or perfusion systems offer distinct advantages over batch culture for large scale in vivo production of biopharmaceuticals. For example, in such systems, cells are constantly provided with fresh nutrients and depleted of toxic byproducts resulting in higher cell densities.

At such high cell densities, the requirements for serum decrease dramatically. For the purpose of downstream processing it is extremely important to minimize the level of serum and thus reduce the major source of contaminant proteins such as albumin, transferrin, serum-derived immunoglobulin, proteases, protease inhibitors, etc., contained in the removed media.

In a state of continuous perfusion, products secreted by the cells which are vulnerable to biodegradation and aggregation at 37° C. can be removed from the bioreactor and transported to a 4° C. environment in readiness for subsequent purification. The rate of product removal from this labile cellular environment is in terms of only hours for perfusion systems as compared to many days and weeks for semibatch systems respectively. This continuous harvesting process minimizes proteolytic degradation and aggregation processes.

However, for most of these systems current methods of harvesting require filters to prevent the loss of the cells through the harvesting. Filters can become clogged causing the shut down of the system. A need exists to develop a more efficient method which allows the harvesting of the desired product without disruption. This need grows progressively more acute as biotechnology and pharmaceutical companies look to cut processing costs. Any elimination of problems which interfere with the continuous operation of these systems would increase their efficiency and subsequently reduce the cost of the biopharmaceutical agents.

SUMMARY OF THE INVENTION

This invention relates to an apparatus for suspending particles in a continuous flow of liquid. The apparatus comprises: 1) an agitation vessel, containing particles suspended in the liquid, wherein the density of each particle is greater than the liquid density; 2) a flow means for the continuous flow of liquid into the agitation vessel; 3) a first variable inlet/outlet means for allowing the periodic flow of a portion of the particle suspension from the agitation vessel to a settling vessel; 4) a second variable inlet/outlet means for allowing the free flow of a portion of the particle suspension between the agitation vessel and the settling vessel; 5) a settling vessel located above the agitation vessel which comprises: i) a body means for allowing the settling of the particles whereby the particles separate from a portion of the liquid; and ii) an outlet means for allowing the removal of liquid; and 6) a vacuum means for drawing a portion of the particle suspension into the settling vessel and for periodically removing a portion of the liquid out of the settling vessel, whereby a continuous flow of the liquid enters into the apparatus and a portion of the liquid periodically exits the apparatus wherein the liquid exiting the apparatus is particle free. In addition, the apparatus of the present invention is suitable for growing particles or for separating liquids of different densities.

The present invention further relates to an apparatus for releasing and collecting liquid containing liquid-soluble substances from particles. The apparatus comprises all of the elements of the apparatus explained above with the additional element of a collection means for the collection of the liquid containing the liquid-soluble substances. Furthermore, the apparatus of the present invention is suitable for producing biological products released from cells and collecting the liquid containing the biological product.

The apparatus of the present invention allows for the continuous flow of new liquid or media to be added to a suspension of particles while allowing the removal of old liquid or media from the suspension; the removed liquid or media being free of the particles. The design of the present invention is such that there is no need for microfilters, hollow fibers, or any other type of filter device and, as such, the problems associated with these devices are avoided.

DETAILED DESCRIPTION OF THE INVENTION

This invention is based upon the discovery that a continuous flow culture apparatus, which does not require filters, could be constructed using a modified inverted Erlenmeyer flask. The modified inverted Erlenmeyer flask, placed above and connected to a conventional cell culture vessel, provided a zone where microcarriers could settle while allowing for the removal of some of the media without removing microcarriers. The apparatus provided for the continuous culturing of anchorage-dependent cells in fresh media while removing media containing proteins expressed by the cells.

Figure 1:
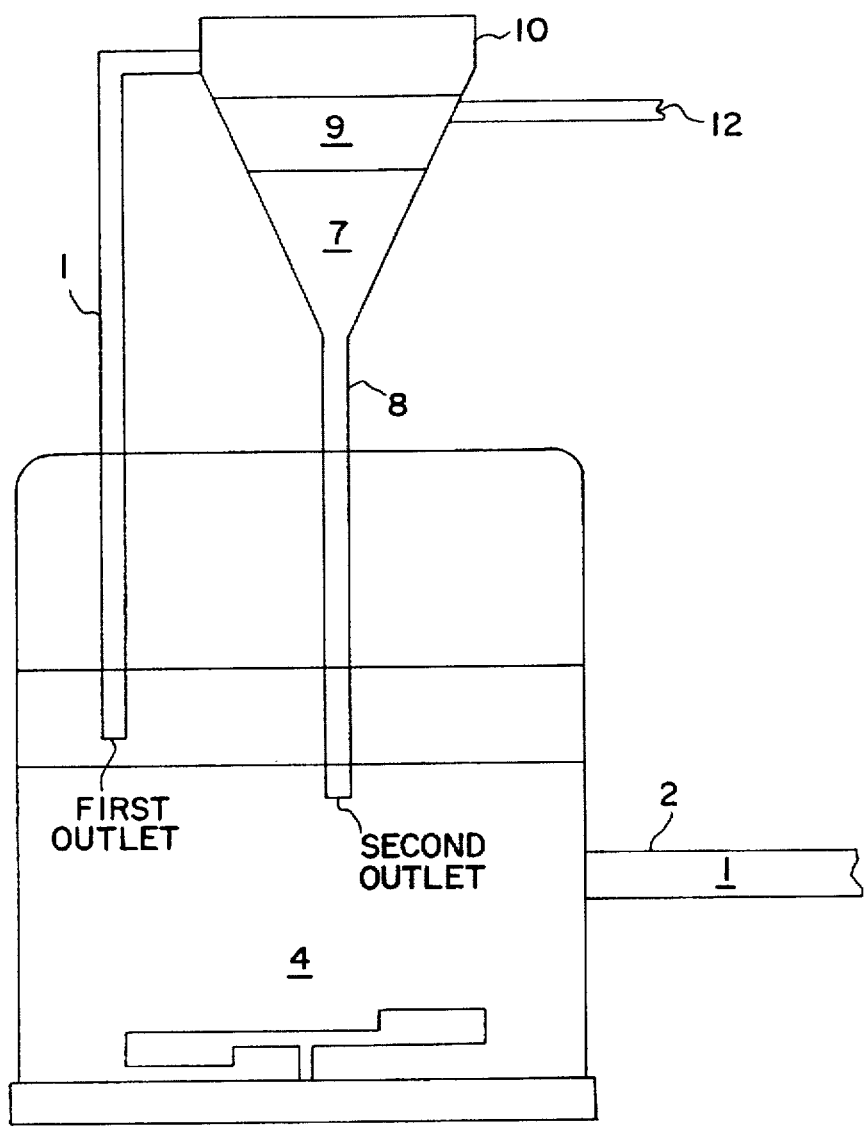
FIG. 1 is a schematic illustration of an embodiment of the present invention.

While the specification concludes with claims particularly pointing out and distinctly claiming the subject matter regarded as forming the present invention, it is believed that the invention will be better understood from the following description in connection with FIG. 1. FIG. 1 is a schematic illustration of one embodiment of the present invention. Liquid (1) enters into agitation vessel 4 through inlet 2 and mixes with particles (3) contained in the agitation vessel. The particles and the liquid are mixed together for a time sufficient to suspend the particles in the liquid to produce particle suspension (5). As the new liquid enters agitation vessel 4 the level of the particle suspension rises to the bottoms of second inlet/outlets 8 and then first inlet/outlet 6. As a result of the level of particle suspension (5) reaching and contacting the bottom of the first inlet/outlet and the outward air flow created by a vacuum device connected to outlet 12, a negative air pressure (i.e., negative relative to the air pressure in the agitation vessel) develops in settling vessel 10. As the negative air pressure in the settling vessel increases, the suspension is drawn up into the inlet/outlets and into settling vessel 10. While in the non-agitated environment of the settling vessel, particles (3) begin to settle to the bottom of settling vessel 10, creating a strata of two zones. The lower zone contains concentrated particle suspension (7) and the upper zone contains particle-free liquid (9). As the negative air pressure continues to increase in the settling vessel the top level of the upper zone migrates to outlet 12. Once the upper zone reaches outlet 12 the outward air pressure draws a portion of liquid (9) out of settling vessel 10. The loss of a portion of the liquid out of the settling vessel has the effect of lowering the level of the particle suspension (5) in the agitation vessel. Once the level in agitation vessel 4 drops below and loses contact with first inlet/outlet 6, the air pressure in settling vessel 10 is neutralized allowing the contents of the settling vessel (i.e., concentrated particle suspension (7) plus a portion of particle free liquid (9)) to empty back into the agitation vessel. This action of forcing the particles that temporarily collected in the settling vessel back into agitation vessel 4, prevents the loss of the particles through the outlet. The above explained cycle then repeats once the level of the particle suspension rises to the bottom and contacts the first variable inlet/outlet due to the accumulation of liquid that collects in agitation vessel 4 as a result of the flow of liquid entering the agitation vessel.

The term "particles" is intended to include any synthetic or biological substance or any substance with a synthetic and biological component. For example, the particles of the present invention include biological cells such as hybridoma cells. In the alternative the particles have a synthetic and biological component, such as anchorage-dependent cells attached to polyacrylamide microcarriers or polymer encapsulated cells.

Any liquid can be used in the apparatus of the present invention. Suitable liquids include aqueous solutions such as nutrient medium, for example Dulbecco's Modified Eagles Medium (Gibco, Grand Island, N.Y.). Particle suspension refers to the random dispersion of particles in a liquid, the dispersion of the particles being caused by an agitation device, such as a propeller. It should be noted that in order for the apparatus of the present invention to function properly each particle needs to have a density greater than the liquid density, i.e., have sufficient density to be able to settle, due to gravitational force, when in a non-agitated environment.

Emulsion refers to the random dispersion of one liquid in another. It should be noted that the liquids need to have different densities in order to subsequently effect separation.

Any vessel mentioned above or herein, must be a container with inner containment walls constructed of an inert material, i.e., a material that will not leach or react when in contact with the particles or liquid used in the present invention. In a one embodiment, vessels with inner containment walls constructed of stainless steel are preferred.

The agitation vessel of the present invention encompasses any vessel equipped with an agitation device. Suitable agitation devices include mechanical means, hydrodynamic means, or ultrasonic means using a conventional bath or probe sonication device. Mechanical means include axial-flow impeller-type mixers such as marine-type mixing propeller or pitched-blade turbine, or radial-flow impellers such as curved-blade turbine or flat-blade turbine. The main criteria for any agitation device used in the apparatus of the present invention is that the portion of the device that comes in contact with the particles should not cause their fracturing or shearing or such action should be kept to a minimum.

The term "flow means" is intended to describe any device capable of causing the continuous flow of liquid into the agitation vessel. The term "vacuum means" is intended to describe any device capable of creating negative air pressure (i.e., air pressure below that which is present in the agitation vessel) in a closed vessel and capable of removing liquid from a vessel. In both cases, suitable devices include peristaltic-type, diaphragm-type, gear-type, piston-type and rotary-lobe type pumps. The main criteria for any pump used for either purpose in the apparatus of the present invention is that the portion of the pump that comes in contact with the liquid should be inert and not react with the liquid by changing or adding to the its composition.

The term "second variable inlet/outlet means" is intended to mean any device which allows for liquid to flow freely, in either direction, between two vessels. Suitable devices include any pipe, tube, hose or any other cylinder with an inner containment wall constructed of inert material such as stainless steel.

The term "first variable inlet/outlet" is intended to mean any device which allows the flow of liquid from the agitation vessel to the settling vessel, as described above, but only in a periodic fashion. This can be accomplished by having the first variable inlet/outlet not extend as far into the agitation vessel as the second variable inlet/outlet means, as shown in FIG. 1. The length differential allows for the negative air pressure to return to the pressure in the agitation vessel when the liquid level in the agitation level is no longer in contact with the first variable inlet/outlet means. The process of periodically allowing negative air pressure to develop in the settling vessel is explained in detail above (see FIG. 1).

In addition, it should be noted that in circumstances where the liquid used in the apparatus of the present invention produces foam, as in the case with some nutrient media, a device (or anti-foamimg agent) to remove the foam from the apparatus or to prevent the foam from entering the first variable inlet/outlet means needs to be used. Foam that forms in the agitation vessel can be drawn up into the settling vessel preventing the proper function of the apparatus. In a preferred embodiment, the apparatus of the present invention the first variable inlet/outlet means includes a collar which prevents foam from entering the first variable inlet/outlet means. The collar can consist of a bell shaped cylinder, with holes drilled at the top, which attaches and extends beyond the bottom of a pipe used as a first variable inlet/outlet means. Suitable collars are constructed of inert material, preferably stainless steel.

The term "settling vessel" refers to any vessel which provides a non-agitated environment apart from the agitation vessel. The settling vessel of the present invention needs to have an inert inner containment wall, as explained above, and a shape which does not prevent particles from returning to the agitation vessel. For example, a suitable settling vessel would be constructed with inner walls of stainless steel and have a conical shape. In a preferred embodiment, the settling vessel is a cylinder with a conical shaped bottom portion and a closed top (see FIG. 1). It should be noted that in order for the settling vessel of the present invention to function properly it needs to be located above the agitation vessel. In addition, the settling vessel has at least one port connected to the second variable inlet/outlet means, at least one port connected to the first variable inlet/outlet means and at least one port connected to the outlet means. In order for any settling vessel to function properly in the apparatus of the present invention any port in the settling vessel that is connected to the first variable inlet/outlet means should be located above any port in the settling vessel connected to the outlet (in the settling vessel), and any port in the settling vessel connected to the second variable inlet/outlet means should be located below the port in the settling vessel connected to the outlet.

The term "liquid-soluble substances" refers to any substance that is soluble in the particular liquid used in the apparatus of the present invention and is generated by the particles. The term "biological products" refers to any substance produced by a biological organism such as cell expressed protein.

The invention will be further illustrated by the following non-limiting Exemplification:

EXEMPLIFICATION

Materials and Methods:

A standard 125 ml Erlenmeyer flask was modified by attaching a ¼ inch diameter glass tubing to the side of the flask just below the top of the flask as inverted (see the Figures). In addition, the neck was extended and narrowed to a ¼ inch diameter.

Cytodex III microcarriers were purchased from Pharmacia, Piscataway, N.J. The microcarriers are spherical objects made of dextran with a diameter of approximately 200 μm. The microcarriers were coated with a layer of porcine collagen to promote cell attachment.

Anchorage-dependent mammalian cells were grown in nutrient medium.

A glass 2 liter vessel purchased from Bellco Glass, Inc. (Vineland N.J.) was used as the agitation vessel. The vessel was equipped with a teflon paddle and magnetic stir bar and connected to mixed gas ($O_2$, $CO_2$, $N_2$) to maintain the pH and dissolved oxygen level of the nutrient media. The movement of the magnetic stir bar was controlled by a magnetic stir bar plate positioned underneath the bottom of the agitation vessel (purchased from Bellco Glass).

A 5 liter glass vessel purchased from Bellco Glass was used as a media supply vessel.

A 10 liter polycarbonate carboy was used as a harvest vessel.

Pumps used were peristaltic-type pumps purchased from Cole-Parmer Instrument Co. (Chicago, Ill.).

Figure 2:
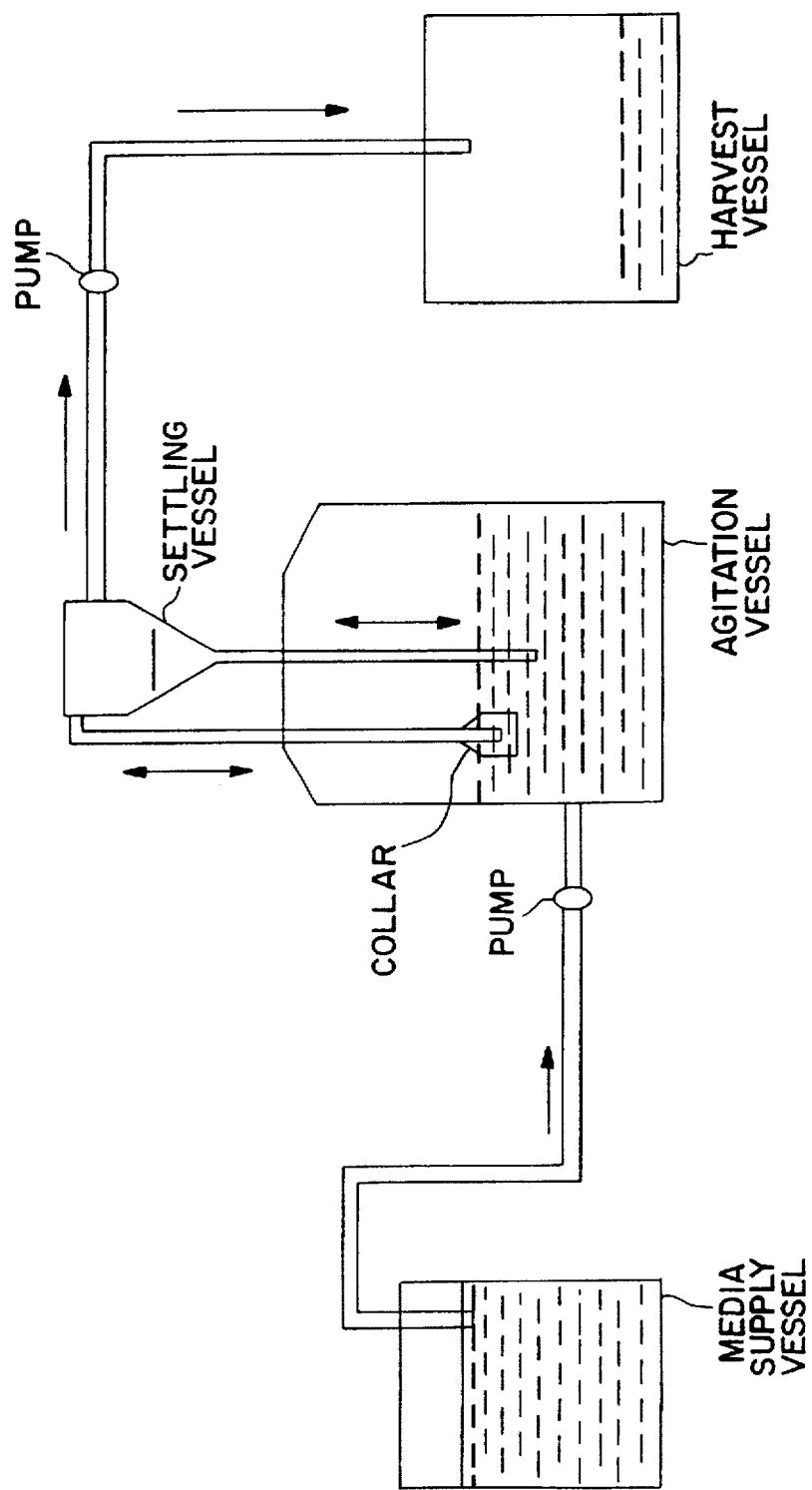
FIG. 2 is a schematic illustration showing a cell culture apparatus with the preferred embodiment of the present invention.

Continuous Cell Culture Apparatus (see FIG. 2):

One liter of media containing microcarriers and anchorage dependent cells were placed into the agitation vessel.

The media supply vessel was connected to the agitation vessel by silicone tubing. A peristaltic pump was positioned between these two vessels to pump fresh nutrient medium into the agitation vessel.

The settling vessel, constructed as explained above, was positioned above the agitation vessel. The pipe extending from the side of the settling vessel was connected to a ¼ inch stainless steel tube which was then inserted into the agitation vessel. In addition, a bell shaped cylinder with holes drilled through the top (i.e., collar) was attached and extended beyond this ¼ inch pipe. Another ¼ inch pipe was connected to the mouth of the inverted Erlenmeyer flask (i.e., settling vessel) and inserted into the agitation vessel running parallel to the other ¼ inch pipe and extending further into the agitation vessel than both said ¼ inch pipe and collar attachment.

The outlet of the settling vessel was connected via silicone tubing to the harvest vessel. A peristaltic pump was positioned between the settling vessel and the harvest vessel to create a vacuum in the settling vessel to draw the microcarrier suspension into the settling vessel and for the removal of media.

Operation of Continuous Cell Culture Apparatus:

The agitation was set at 30 rpm to maintain the microcarriers in suspension.

Dissolved oxygen was maintained between 10 and 20 mm HG by adjusting the percent oxygen in the overlay.

The pump positioned between the media supply vessel and the agitation vessel was set at one liter per day rate.

The pump positioned between the settling vessel and the harvest vessel was set at slightly faster than one liter per day rate.

The operation of the apparatus was maintained for 21 days and the agitation of the microcarriers was not suspended for the duration.

Comparison with Batch-Type Procedure:

Cells grown as described above were compared with cells grown by a conventional batch type method (fedbatch) for the same time frame.

The apparatus used for the batch method was constructed similarly to the agitation vessel described above, i.e., a glass 2 liter vessel equipped with a teflon paddle and magnetic stir bar and connected to mixed gas. As in the above described apparatus the magnetic stir bar was controlled by a magnetic stir bar plate, however, the batch apparatus was not connected to an inverted Erlenmeyer flask (i.e., settling vessel) as explained above.

The batch cells were maintained by replacing approximately 80% of the nutrient media every 24 hours. The media was replaced by stopping the agitation caused by the magnetic stir bar, allowing the microcarrier attached cells to settle, aspirating off and replacing 80% of the nutrient media with fresh media and starting the agitation of the microcarriers again.

Figure 3:
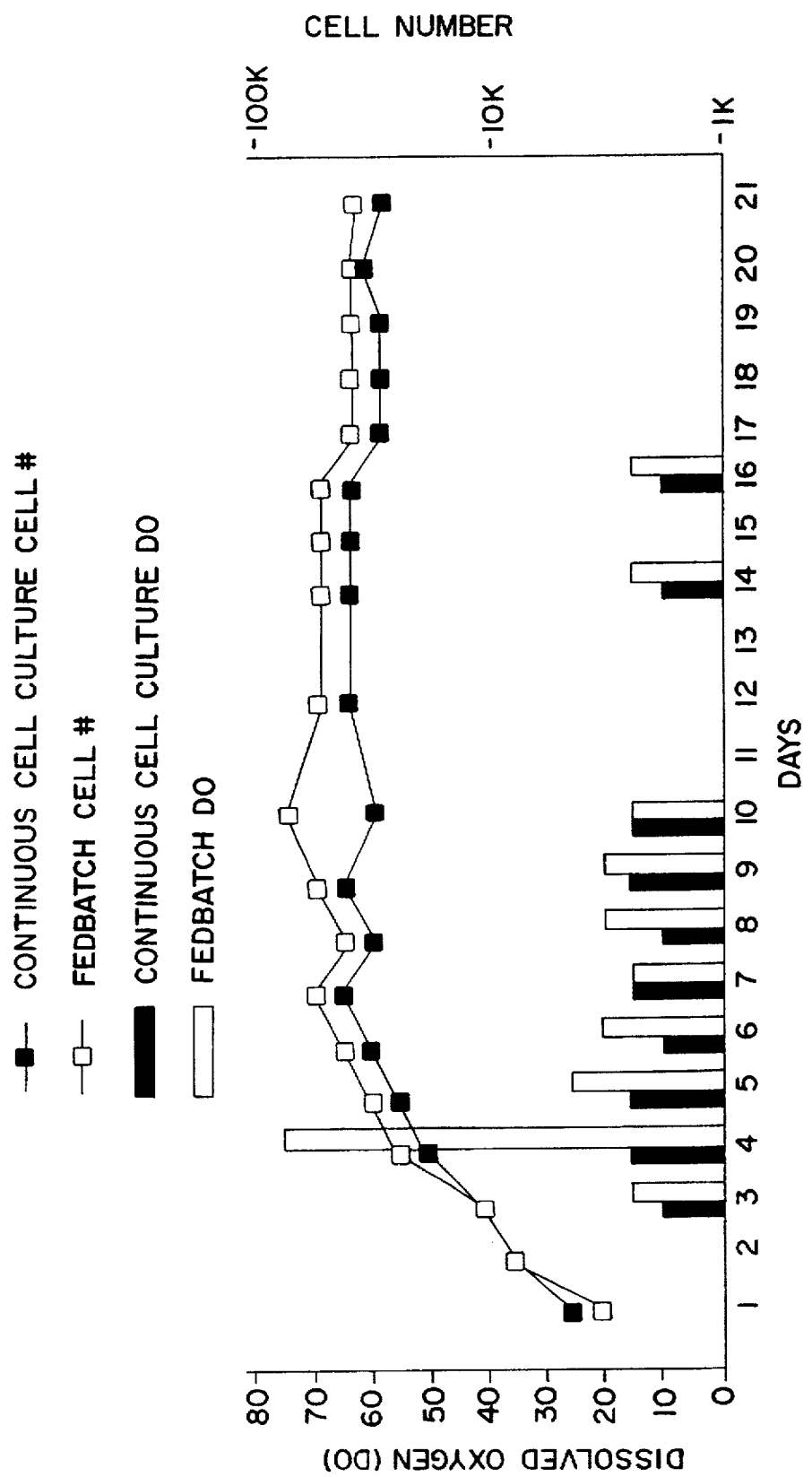
FIG. 3 is a graph showing the comparison of cells grown in a cell culture apparatus with the preferred embodiment of the present invention versus cells grown in a conventional batch type procedure.

FIG. 3 is a graph that compares the cells grown in the apparatus explained in detail above and the cells grown by the batch method. Because of the physical setup of the continuous settling apparatus there was no port available on the agitation vessel for gas entry therefore there was an oxygen limitation which limited cell number. There problem is easily rectified by modifying the agitation vessel by creating a port for gas entry.

Equivalents

Those skilled in the art will recognize, or be able to ascertain, using no more than routine experimentation many equivalents to the specific embodiments of the invention described herein. Such equivalents are intended to be encompassed by the following claims:

We claim:

1. A continuous settling apparatus, comprising:
   a. an agitation vessel, comprising:
      i. a first hollow body;
      ii. an agitation device capable of maintaining particles suspended in a liquid; and
      iii. a flow means for the continuous flow of the liquid into the agitation vessel;
      iv. a first and a second pipe and outlet for allowing the free flow of a portion of the particle suspension from and to the agitation vessel wherein the second outlet is below the first outlet within the first hollow body; and b. a settling vessel located above the liquid level in the agitation vessel and in liquid communication with the agitation vessel via the first and second pipes comprising:
  i. a second hollow body wherein the shape of the second hollow body allows for the settling of the particles from a portion of the liquid;
  ii. a third outlet for allowing the removal of a portion of the separated liquid from the settling vessel;
  iii. a vacuum means, connected to the third outlet, for creating a vacuum in the settling vessel sufficient to draw a portion of the particle suspension into the settling vessel from the agitation vessel when the liquid level in the agitation vessel is at or above the first outlet and for removing a portion of the liquid out of the settling vessel when the liquid reaches the third outlet; and
  iv. a first and a second inlet connected to the first and second pipes, respectively, for allowing the free flow of a portion of the particle suspension from the settling vessel when the liquid level in the agitation vessel is below the first outlet;

whereby a continuous flow of the liquid enters into the agitation vessel and a portion of the liquid periodically reaches the third outlet and exits the settling vessel wherein the liquid exiting is particle free.

2. The apparatus of claim 1 wherein the settling vessel has a conical shape.

3. An apparatus for separating liquids of different densities, comprising:
  a. an agitation vessel, comprising:
    i. a first hollow body;
    ii. an agitation device capable of producing an emulsion consisting of two liquids comprising a first liquid with a density greater than a second liquid;
    iii. a flow means for the continuous flow of the second liquid into the agitation vessel; and
    iv. a first and a second pipe and outlet for allowing the free flow of a portion of the emulsion from and to the agitation vessel wherein the second outlet is below the first outlet within the first hollow body; and
  b. a settling vessel located above the emulsion level in the agitation vessel and in liquid communication with the agitation vessel via the first and second pipes comprising:
    i. a second hollow body wherein the shape of the second hollow body allows for the settling of the first liquid from the second liquid, thereby separating the liquids;
    ii. a third outlet for allowing the removal of the second liquid;
    iii. a vacuum means connected to the third outlet for creating a vacuum in the settling vessel sufficient to draw a portion of the emulsion into the settling vessel from the agitation vessel when the emulsion level in the agitation vessel is at or above the first outlet and for removing the second liquid out of the settling vessel when the second liquid reaches the third outlet: and
    iv. a first and second inlet connected to the first and second pipes, respectively, for allowing the free flow of a portion of the particle suspension from the settling vessel when the emulsion level in the agitation vessel is below the first outlet;

whereby a continuous flow of the second liquid enters into the agitation vessel and the second liquid periodically exits the settling vessel when the level of the second liquid reaches the third outlet wherein the second liquid is free of the first liquid.

4. The apparatus of claim 3 wherein the settling vessel has a conical shape.

5. An apparatus for growing cells adhered to particles in a continuous-flow liquid media culture, comprising:
  a. an agitation vessel, comprising;
    i. a first hollow body;
    ii. an agitation device capable of maintaining the particles suspended in media;
    iii. a flow means for the continuous flow of media into the agitation vessel;
    iv. a first and a second pipe and outlet for allowing the free flow of a portion of the particle suspension from and to the agitation vessel wherein the second outlet is below the first outlet within the first hollow body; and
  b. a settling vessel located above the media level in the agitation vessel and in liquid communication with the agitation vessel via the first and second pipes comprising:
    i. a second hollow body wherein the shape of the second hollow body allows for the settling of the particles from a portion of the media;
    ii. a third outlet for allowing the removal of media;
    iii. a vacuum means for creating a vacuum sufficient to draw a portion of the particle suspension into the settling vessel from the agitation vessel when the media level in the agitation vessel is at or above the first outlet and for removing the media when the media reaches the third outlet; and
    iv. a first and a second inlet connected to the first and second pipes, respectively, for allowing the free flow of a portion of the particle suspension from the settling vessel when the media level in the agitation vessel is below the first outlet;

whereby a continuous flow of the media enters into the agitation vessel and a portion of the media periodically exits the settling vessel when the media level reaches the third outlet wherein the media exiting the is particle free.

6. The apparatus of claim 5 wherein the settling vessel has a conical shape.

7. An apparatus for releasing liquid-soluble substances from particles and collecting liquid containing the liquid-soluble substances, comprising:
  a. an agitation vessel, comprising;
    i. a first hollow body;
    ii. an agitation device capable of maintaining particles suspended in liquid;
    iii. a flow means for the continuous flow of the liquid into the agitation vessel; and
    iv. a first and a second pipe and outlet for allowing the free flow of a portion of the particle suspension from and to the agitation vessel wherein the second outlet is below the first outlet within the first hollow body; and
  b. a settling vessel located above the liquid level in the agitation vessel and in liquid communication with the agitation vessel via the first and second pipes, comprising:
    i. a second hollow body wherein the shape of the second hollow body allows for the settling of the particles from a portion of the liquid, whereby the separated liquid contains liquid-soluble substances released from the particles;

ii. a third outlet for allowing the removal of a portion of the separated liquid;

iii. a vacuum means connected to the third outlet for creating a vacuum in the settling vessel sufficient to draw a portion of the particle suspension into the settling vessel from the agitation vessel when the liquid level in the agitation vessel is at or above the first outlet and for removing a portion of the separated liquid out of the settling vessel when the liquid reaches the third outlet; and iv. a first and a second inlet connected to the first and second pipes, respectively, for allowing the free flow of a portion of the particle suspension from the settling vessel when the liquid level in the agitation vessel is below the first outlet; and c. a collection vessel, comprising:

i. a third hollow body; and ii. an inlet means for allowing the collection of liquid in the collection vessel from the settling vessel, whereby a continuous flow of the liquid enters into the agitation vessel and the separated liquid periodically exits the settling vessel when the separated liquid level reaches the third outlet and the separated liquid is collected in the collection vessel wherein the collected separated liquid contains liquid-soluble substances released from the particles and is particle free.

8. The apparatus of claim 7 wherein the settling vessel has a conical shape.

9. An apparatus for producing and collecting biological products released from cells attached to particles, comprising:

a. an agitation vessel, comprising:

i. a first hollow body;

ii. an agitation device capable maintaining particles suspended in a media;

iii. a flow means for the continuous flow of media into the agitation vessel; sand iv. a first and a second pipe and outlet for allowing the free flow of a portion of the particle suspension from and to the agitation vessel wherein the second outlet is below the first outlet within the first hollow body; and b. a settling vessel located above the media level in the agitation vessel and in liquid communication with the agitation vessel via the first and second pipes, comprising:

i. a second hollow body wherein the shape of the second hollow body allows for the settling of the particles from a portion of the media, whereby the separated media contains biological product released from the cells attached to the particles;

ii. a third outlet for allowing the removal of a portion of the separated media;

iii. a vacuum means connected to the third outlet for creating a vacuum sufficient to draw a portion of the particle suspension into the settling vessel from the agitation vessel when the liquid level in the agitation vessel is at or above the first outlet and for removing the separated media out of the settling vessel when the separated media reaches the third outlet; and iv. a first and a second inlet connected to the first and second pipes, respectively, for allowing the free flow of a portion of the particle suspension from the settling vessel when the liquid level in the agitation vessel is below the first outlet; and c. a collection vessel, comprising:

i. a third hollow body; and ii. an inlet for allowing the collection of the separated media in the collection vessel, whereby a continuous flow of the media enters into the agitation vessel and the separated media periodically reaches the third outlet and exits the settling vessel and the separated media is collected in the collection vessel wherein the collected separated media contains biological product released from the cells attached to the particles and is particle free.

10. The apparatus of claim 9 wherein the settling vessel has a conical shape.

11. A continuous settling apparatus, comprising:

a. an agitation vessel, comprising;

i. a hollow body; and ii. an agitation device;

b. a settling vessel located above the liquid level in the agitation vessel, comprising:

i. a conical shaped body wherein the body is aligned vertically, with the narrow portion being the bottom portion;

ii. at least one pipe exiting a first port on the side portion of the body of the settling vessel, being connected to a second port on the body of the agitation vessel and the pipe extending into the agitation vessel;

iii. at least one pipe exiting a third port on the bottom portion of the body, being connected to a fourth port on the body of the agitation vessel and extending further into the agitation vessel than the pipe connected to the first and second port; and iv. at least one pipe exiting a fifth port on the side portion of the body of the settling vessel, the fifth port located below the first port and being connected to a vacuum means.

12. The apparatus of claim 11 wherein the pipe connected to the first and second port has a bell-shaped collar attached to the end of the portion of the pipe that extends into the agitation vessel.

13. An apparatus for growing cells attached to particles, comprising:

a. an agitation vessel, comprising;

i. a hollow body; and ii. an agitation device; and b. a settling vessel located above the liquid level in the agitation vessel, comprising:

i. a conical shaped body wherein the body is aligned vertically, with the narrow portion being the bottom portion;

ii. at least one pipe exiting a first port on the side portion of the body of the settling vessel being connected to a second port on the body of the agitation vessel and extending into the agitation vessel;

iii. at least one pipe exiting a third port on the bottom portion of the body of the settling vessel, being connected to a fourth port and extending further into the agitation vessel than the pipe connected to the first and second port; and iv. at least one pipe exiting a fifth port on the side portion of the body of the settling vessel, the fifth port located below the first port and being connected to a vacuum means.

14. The apparatus of claim 13 wherein the pipe connected to the first and second port has a bell-shaped collar attached to the end of the portion of the pipe that extends into the agitation vessel.

15. An apparatus for growing cells in a continuous-flow liquid media culture, comprising:

a. an agitation vessel, comprising;
   i. a first hollow body;
   ii. an agitation device capable of maintaining the cells suspended in media;
   iii. a flow means for the continuous flow of media into the agitation vessel;
   iv. a first and second pipe and outlet for allowing the free flow of a portion of the cell suspension from and to the agitation vessel wherein the second outlet is below the first outlet within the first hollow body; and
b. a settling vessel located above the liquid level in the agitation vessel and in liquid communication with the agitation vessel via the first and second pipes, comprising:
   i. a second hollow body wherein the shape of the second hollow body allows for the settling of the cells from a portion of the media; and
   ii. a third outlet for allowing the removal of media;
   iii. a vacuum means connected to the third outlet for creating a vacuum in the settling vessel sufficient to draw a portion of the cell suspension into the settling vessel when the media level in the agitation vessel is at or above the first outlet and for removing the media when the media reaches the third outlet; and
   iv. a first and a second inlet connected to the first and second pipes, respectively, for allowing the free flow of a portion of the cell suspension from the settling vessel when the media level in the agitation vessel is below the first outlet, whereby a continuous flow of the media enters into the agitation vessel and a portion of the media periodically exits the settling vessel when the media reaches the third outlet wherein the media exiting the settling vessel is cell free.

16. An apparatus for growing cells in liquid media, comprising:
a. an agitation vessel, comprising;
   i. a hollow body; and
   ii. an agitation device; and
b. a settling vessel located above the liquid level in the agitation vessel, comprising:
   i. a conical shaped body wherein the body is aligned vertically, with the narrow portion being the bottom portion;
   ii. at least one pipe exiting a first port on the side portion of the body of the settling vessel being connected to a second port on the body of the agitation vessel and extending into the agitation vessel;
   iii. at least one pipe exiting a third port on the bottom portion of the body of the settling vessel, being connected to a fourth port and extending further into the agitation vessel than the pipe connected to the first and second port; and
   iv. at least one pipe exiting a fifth port on the side portion of the body of the settling vessel, the fifth port located below the first port and being connected to a vacuum means.

* * * * *